United States Patent [19]

Niwa et al.

[11] Patent Number: 4,685,919
[45] Date of Patent: Aug. 11, 1987

[54] ARTIFICIAL JOINT

[75] Inventors: Shigeo Niwa; Kazuo Kondo; Katsutoshi Betsuki, all of Aichi, Japan

[73] Assignee: NGK Spark Plug Co., Ltd., Aichi, Japan

[21] Appl. No.: 839,575

[22] Filed: Mar. 14, 1986

[30] Foreign Application Priority Data

Mar. 14, 1985 [JP] Japan ............................ 60-36914[U]
Mar. 14, 1985 [JP] Japan ............................ 60-36915[U]
Mar. 18, 1985 [JP] Japan ............................ 60-38714[U]

[51] Int. Cl.[4] ........................ A61F 2/42; A61F 2/30
[52] U.S. Cl. ........................................ 623/21; 623/18
[58] Field of Search ........................ 623/21, 20, 18, 16

[56] References Cited

U.S. PATENT DOCUMENTS

| 3,760,427 | 9/1973 | Schultz | 623/20 |
| 3,869,729 | 3/1975 | Attenborough | 623/20 |
| 3,946,445 | 3/1976 | Bentley et al. | 623/21 X |
| 3,990,118 | 11/1976 | Strickland et al. | 623/21 X |
| 4,011,603 | 3/1977 | Steffee | 623/21 |
| 4,059,854 | 11/1977 | Laure | 623/21 |
| 4,213,208 | 7/1980 | Marne | 623/21 |
| 4,257,128 | 3/1981 | Scales et al. | 623/20 |

FOREIGN PATENT DOCUMENTS 2501128 7/1976 Fed. Rep. of Germany ........ 623/20

Primary Examiner—Ronald L. Frinks
Attorney, Agent, or Firm—Finnegan, Henderson, Farabow, Garrett and Dunner

[57] ABSTRACT

An artificial joint for joining two bones comprises first and second members each including a shank portion for attachment to one of the bones and a mating member adapted to contact the mating member of the other member to enable smooth rotation through a predetermined angle in only two directions.

10 Claims, 46 Drawing Figures

ARTIFICIAL JOINT

BACKGROUND OF THE INVENTION

1. Field of the Invention:

This invention relates to an artificial joint and, more particularly, to an artificial joint for a finger or the like.

2. Description of the Prior Art:

There is known an artificial joint comprising a spherical articulatory member and a member having a complementarily concave surface in which the spherical member is fitted. There is also known an artificial joint comprising a pair of articulatory members each having a hole through which a pin extends to, join them. There is also known an artificial joint comprising members formed from a soft material, such as a resin or rubber. All of these joints have, however, their own drawbacks.

The artificial joint including a spherical member is required to have a very accurate shape in order to be capable of flexing smoothly. The manufacture of an accurately shaped joint is very difficult and requires a great deal of time and labor. This type of joint cannot be used for a finger or any other part of the body that is usually required to move only in two directions in a single plane, since one of its members is rotatable in all directions relative to the other.

The joint including a pin has the advantage that the pin restricts the articulatory members to rotation in only two directions. The pin, however, adds to the number of the parts forming the joint and increases the time required for assembling the joint for implantation. Moreover, the pin must have such a small diameter that a load bearing on it presents serious problems from the standpoint of durability and wear resistance.

The formation of sliding portions from a soft material also has a number of drawbacks. They are movable only to a limited extent and certain muscular force is required for maintaining them in their flexed positions. They are not satisfactory in fatigue strength.

SUMMARY OF THE INVENTION

An object of this invention is an artificial joint that is slidable only in two directions. Another object of the present invention is an artificial joint that is strong and durable.

These and other objects are attained by an artificial joint comprising a first member adapted for attachment to a first bone and a second member adapted for attachment to a second bone at a variable angle to the first member, the first member includes a first shank portion adapted to be set in the first bone and a first sliding portion formed at one end of the first shank portion and having an outwardly protruding portion, the second member includes a second shank portion adapted to be set in the second bone and a second sliding portion having a surface contacting the peripheral surface of the first sliding portion and a recess formed therein for receiving the protruding portion of the first shank portion.

The peripheral surface of the first sliding portion is in rolling contact with the surface of the second sliding portion to allow the joint to flex. The two shank portions are, therefore, slidable only in two directions. The contact of the two sliding portions with each other provides a joint which works smoothly and effectively.

DESCRIPTION OF THE PREFERRED EMBODIMENTS

Figure 1A:
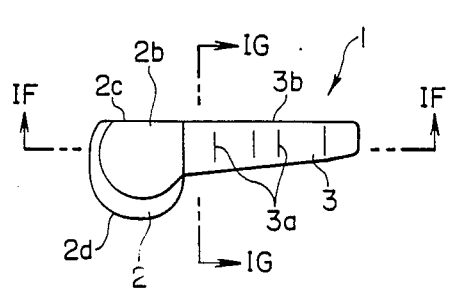
FIG. 1A is a front elevational view of a first member in an artificial joint for a finger according to a first embodiment of the present invention, the first member being adapted for location near the palm.
Figure 1B:
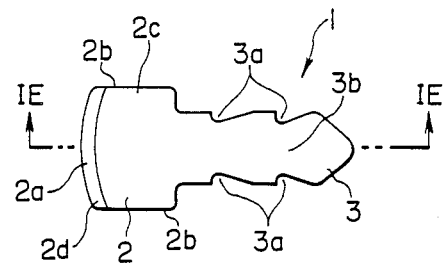
FIG. 1B is a top plan view of the member of FIG. 1A.
Figure 1C:
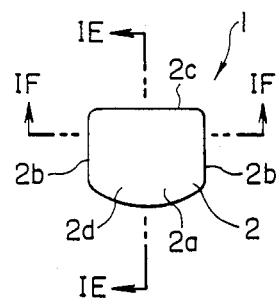
FIG. 1C is a left side elevational view of the member of FIG. 1A.
Figure 1D:
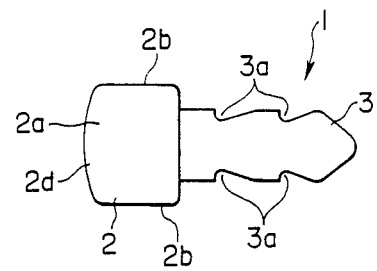
FIG. 1D is a bottom plan view of the member of FIG. 1A.
Figure 1E:
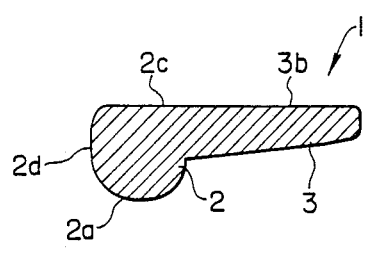
FIG. 1E is a sectional view taken along the line IE—IE of FIGS. 1B and 1C.
Figure 1F:
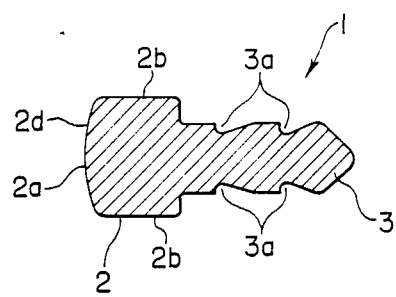
FIG. 1F is a sectional view taken along the line IF—IF of FIGS. 1A and 1C.
Figure 1G:
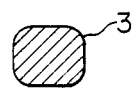
FIG. 1G is a sectional view taken along the line IG—IG of FIG. 1A.
Figure 2A:
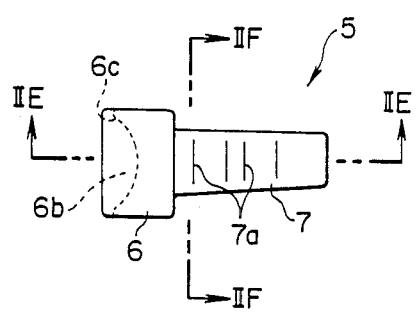
FIG. 2A is a front elevational view of a second member in the artificial joint according to the first embodiment of the present invention, the second member being adapted for location near the tip of the finger.
Figure 2B:
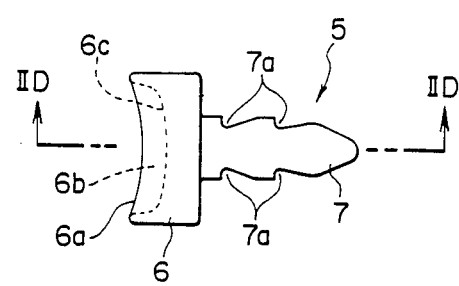
FIG. 2B is a top plan view of the member of FIG. 2A.
Figure 2C:
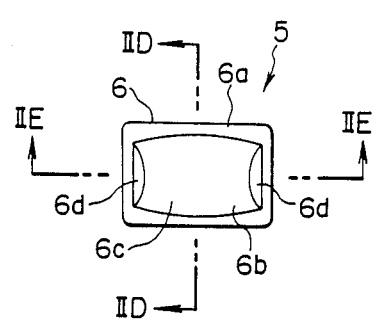
FIG. 2C is a left side elevational view of the member of FIG. 2A.
Figure 2D:
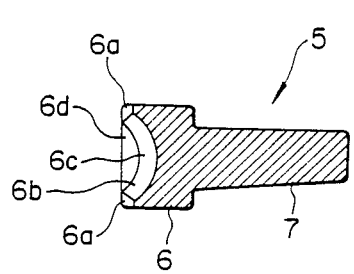
FIG. 2D is a sectional view taken along the line IID—IID of FIG. 2B or 2C.
Figure 2E:
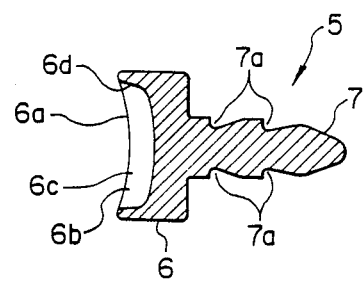
FIG. 2E is a sectional view taken along the line IIE—IIE of FIG. 2A or 2C.
Figure 2F:
FIG. 2F is a sectional view taken along the line IIF—IIF of FIG. 2A.

A number of preferred embodiments of this invention will now be described with reference to the drawings. Referring first to FIGS. 1A to 4, there is shown an artificial joint for a finger according to a first embodiment of the present invention. It includes a first member that is shown by way of example in FIGS. 1A to 1G. The first member 1 comprises a sliding portion 2 and a shank portion 3. The sliding portion 2 has a substantially columnar shape, but its middle portion 2a is larger in diameter than its opposite end portions 2b. It has a flat surface 2c lying in parallel to its longitudinal axis. The flat surface 2c has an edge to which one end of the shank portion 3 is joined. The sliding portion 2 has an arcuate outer peripheral surface 2d having a substantially equal radius of curvature throughout its longitudinal axis.

The shank portion 3 comprises a tapered bar having a substantially square cross section and is rounded at each corner. It has a pair of opposite surfaces each formed with a pair of grooves 3a having triangular cross sections. One of two walls defining the triangular cross section of each groove 3a is located closer to the sliding portion 2 than the other is, and lies substantially at right angles to the longitudinal axis of the shank portion 3. The shank portion 3 also has a flat surface 3b that is flush with the flat surface 2c of the sliding portion 2. The shank portion 3 is adapted for insertion into a hole formed in the marrow of a finger bone to secure the joint to the bone.

The artificial joint also includes a second member that is shown by way of example in FIGS. 2A to 2F. The second member 5 also comprises a sliding portion 6 and a shank portion 7. The sliding portion 6 has substantially the shape of a rectangular parallelepiped and one of its largest surfaces is joined to the shank portion 7. The surface of the sliding portion 6 which is remote from the shank portion 7 is an inwardly curved surface 6a having its curve along its longer sides. The curved surface 6a has a recess or concavity 6b that is complementary to the outer peripheral surface 2d of the sliding portion 2 in the first member. The concavity 6b is defined by an inner surface 6c that is curved in a direction perpendicular to that of the curvature of the curved surface 6a, and a pair of outwardly deflected opposite edge surfaces 6d.

The shank portion 7 comprises a tapered bar having a substantially square cross section that is rounded at each corner. It has a pair of opposite surfaces each formed with a pair of grooves 7a having triangular cross sections. The grooves 7a are preferably identical in shape to the grooves 3a in the shank portion 3 of the first member 1. The shank portion 7 is used for the same purpose as that for which the shank portion 3 of the first member 1 is used.

Figure 3:
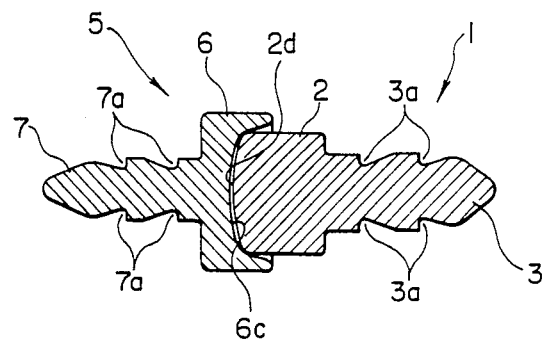
FIG. 3 is a longitudinal sectional view of the members of FIGS. 2A and 2B put together.
Figure 4:
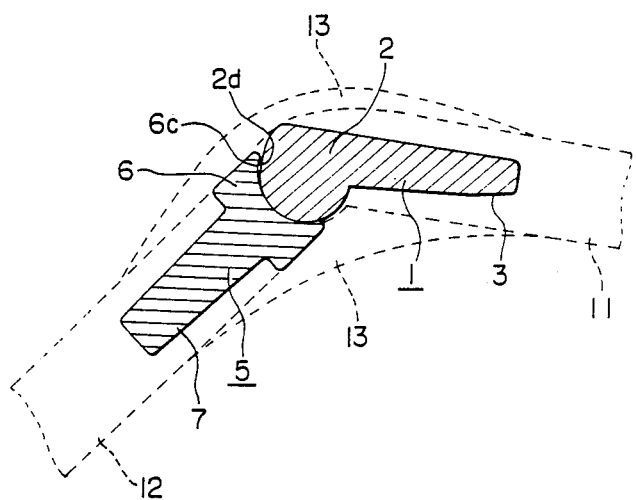
FIG. 4 is a longitudinal sectional view of the members of FIGS. 2A and 2B put together and attached to the bones in the finger.
Figure 5A:
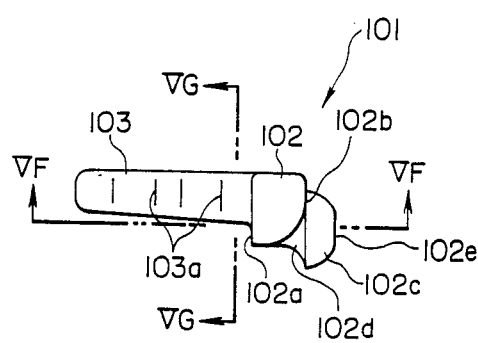
FIG. 5A is a front elevational view of a first member in an artificial joint according to a second embodiment of the present invention.
Figure 5B:
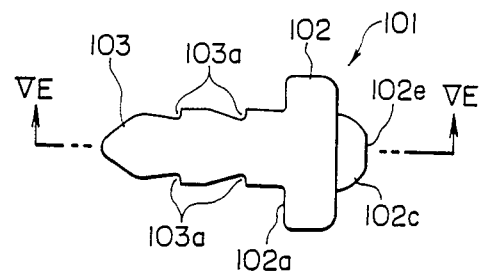
FIG. 5B is a top plan view of the member of FIG. 5A.
Figure 5C:
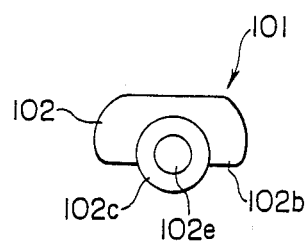
FIG. 5C is a right side elevational view of the member of FIG. 5A.
Figure 5D:
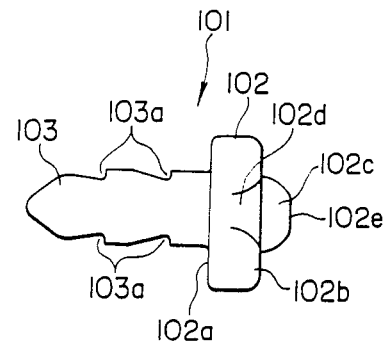
FIG. 5D is a bottom plan view of the member of FIG. 5A.
Figure 5E:
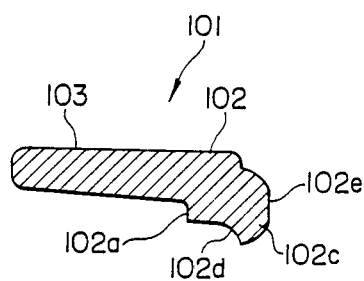
FIG. 5E is a sectional view taken along the line VE—VE of FIG. 5B.
Figure 5F:
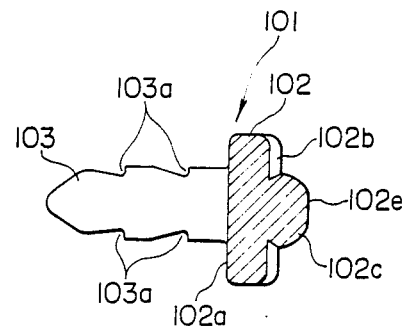
FIG. 5F is a sectional view taken along the line VF—VF of FIG. 5A.
Figure 5G:
FIG. 5G is a sectional view taken along the line VG—VG of FIG. 5A.
Figure 6A:
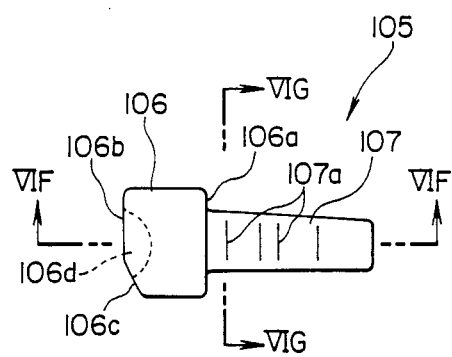
FIG. 6A is a front elevational view of a second member in the artificial joint according to the second embodiment of the present invention.
Figure 6B:
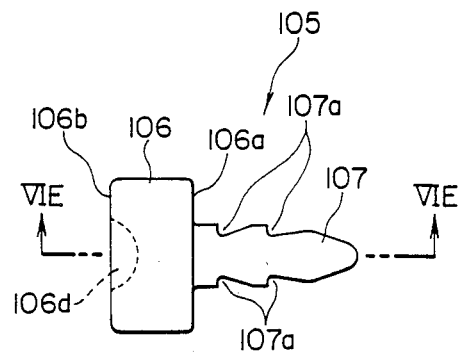
FIG. 6B is a top plan view of the member of FIG. 6A.
Figure 6C:
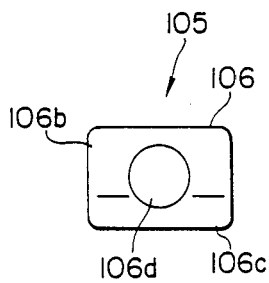
FIG. 6C is a left side elevational view of the member of FIG. 6A.
Figure 6D:
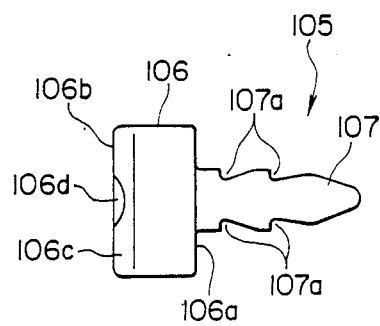
FIG. 6D is a bottom plan view of the member of FIG. 6A.
Figure 6E:
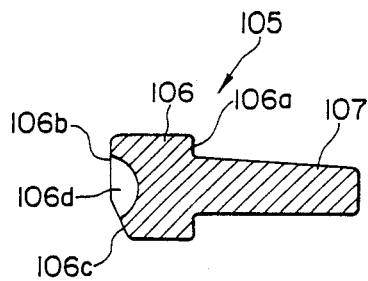
FIG. 6E is a sectional view taken along the line VIE—VIE of FIG. 6B.
Figure 6F:
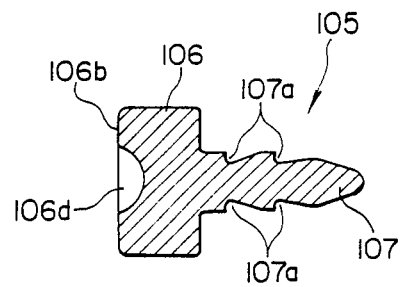
FIG. 6F is a sectional view taken along the line VIF—VIF of FIG. 6A.
Figure 6G:
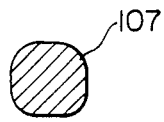
FIG. 6G is a sectional view taken along the line VIG—VIG of FIG. 6A.

The first and second members 1 and 5 are assembled to form one of the finger joints as shown in FIGS. 3 and 4. Referring to FIG. 3, the sliding portion 2 of the first member 1 is fitted into the concavity 6b of the second member 5. The outer peripheral surface 2d of the sliding portion 2 is in intimate contact with the inner surface 6c of the concavity 6b. The surfaces 2d and 6c are slidable on each other and, therefore, the shank portions 3 and 7 have therebetween an angle of flexure which is variable in a single plane.

FIG. 4 shows the first and second members 1 and 5 attached to the bones of a finger. That part of FIG. 4 which shows the first member 1 is identical to FIG. 1E and that part which shows the second member 5 is identical to FIG. 2D. The bones are shown at 11 and 12, and a ligament at 13. The shank portion 3 of the first member 1 is set in the marrow of the bone 11, and the shank portion 7 of the second member 5 is set in the marrow of the bone 12. The bones 11 and 12 urge the first and second members 1 and 5 against each other and maintain the surfaces 2d and 6c in contact with each other.

The artificial joint as hereinabove described by way of example is simple in construction and easy to manufacture. It is smoothly slidable only in two directions within an appropriate angle and is, therefore, a particularly suitable joint for a finger. It has only two contact surfaces 2d and 6c and, therefore, a very high degree of strength and durability. It is very easy to assemble during a surgical operation, since it is sufficient to fit the outer peripheral surface 2d of the first member in the inner surface 6c of the second member.

Because the walls of the triangular grooves 3a and 7a in the shank portions 3 and 7 are substantially perpendicular to the axes of the shank portions 3 and 7, respectively, they receive a substantially perpendicular force from the bones. This feature promotes the growth of the bone tissue and the connection of the joint to the bones. The walls of the grooves 3a and 7a need not be substantially perpendicular to the axes of the shank portions, however, but can be formed to define an acute angle without causing the joint to lose the advantages as hereinabove described.

Reference is now made to FIGS. 5A to 8 showing a second embodiment of the present invention. It includes a first member that is shown by way of example in FIGS. 5A to 5G. The first member 101 comprises a sliding portion 102 and a shank portion 103. The sliding portion 102 has a hemispherical protrusion 102c projecting from a support 102d in the vicinity of the center of the outer surface 102b of a column forming the sliding portion 102. The protrusion 102c has an axis that is substantially parallel to the longitudinal axis of the shank portion 103. The support 102d is smaller in diameter than the protrusion 102c. The protrusion 102c has a flat top surface 102e.

The joint also includes a second member that is shown by way of example in FIGS. 6A to 6G. The second member 105 has an outer surface 105b designed for engaging the first member 101. It has substantially the shape of a rectangular parallelepiped. One of the longer edges of the surface 106b has a beveled surface 106c. The outer surface 106b is formed in its center with a concavity 106d defining a substantially hemispherical inner surface. When the first and second members are bent relative to each other, the outer surface 102b of the first member slidingly rolls on the surfaces 106b and 106c of the second member, while the protrusion 102c stays in the concavity 106d throughout any such rolling movement.

Figure 7:
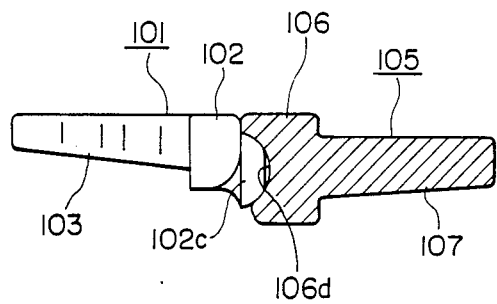
FIG. 7 is a view showing in its assembled form the joint according to the second embodiment of the present invention.
Figure 8:
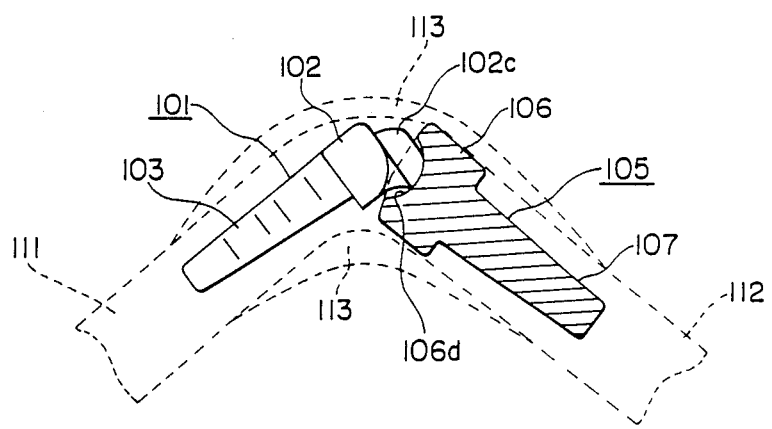
FIG. 8 is a view showing in its flexed position the joint of FIG. 7 attached to finger bones.
Figure 9A:
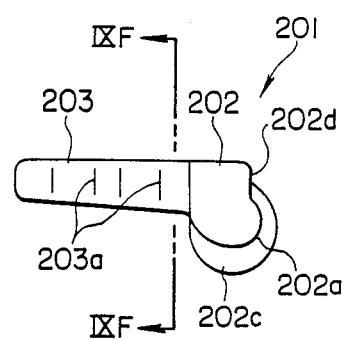
FIG. 9A is a front elevational view of a first member in an artificial joint according to a third embodiment of the present invention.
Figure 9B:
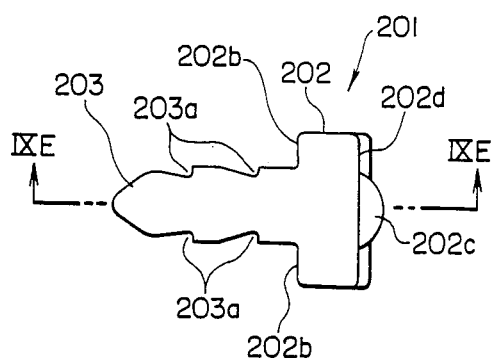
FIG. 9B is a top plan view of the member of FIG. 9A.
Figure 9C:
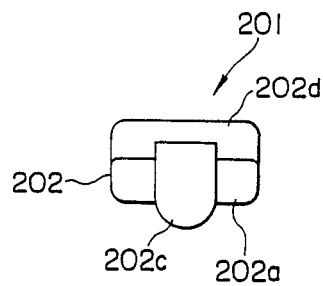
FIG. 9C is a right side elevational view of the member of FIG. 9A.
Figure 9D:
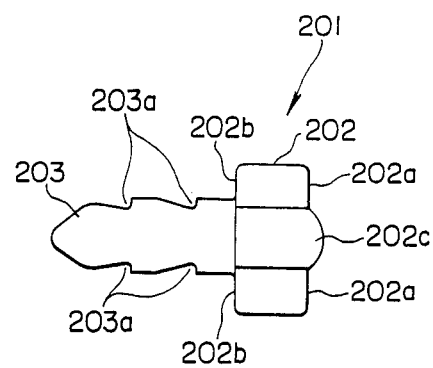
FIG. 9D is a bottom plan view of the member of FIG. 9A.
Figure 9E:
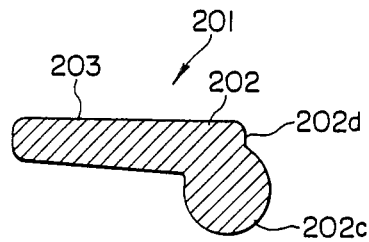
FIG. 9E is a sectional view taken along the line IXE—IXE of FIG. 9B.
Figure 9F:
FIG. 9F is a sectional view taken along the line IXF—IXF of FIG. 9A.
Figure 10A:
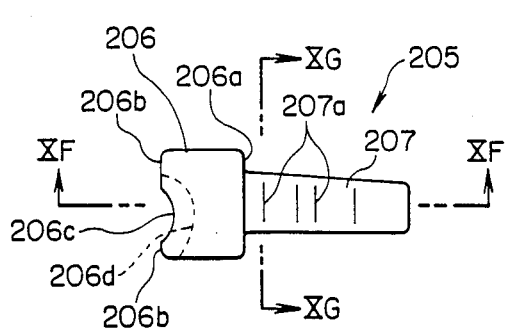
FIG. 10A is a front elevational view of a second member in the artificial joint according to the third embodiment of the present invention.
Figure 10B:
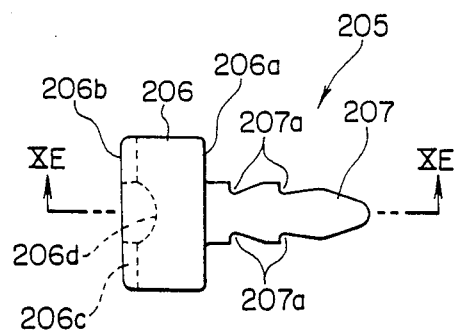
FIG. 10B is a top plan view of the member of FIG. 10A.
Figure 10C:
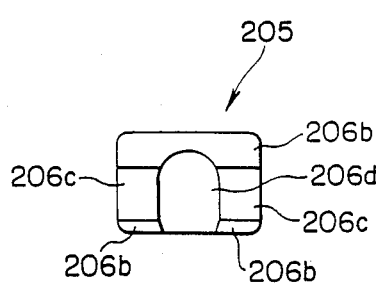
FIG. 10C is a left side elevational view of the member of FIG. 10A.
Figure 10D:
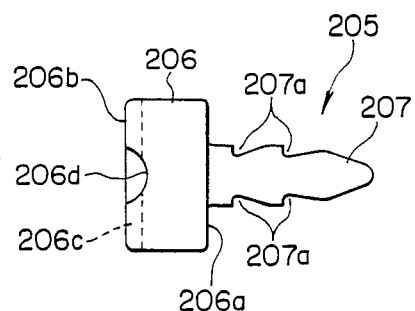
FIG. 10D is a bottom plan view of the member of FIG. 10A.
Figure 10E:
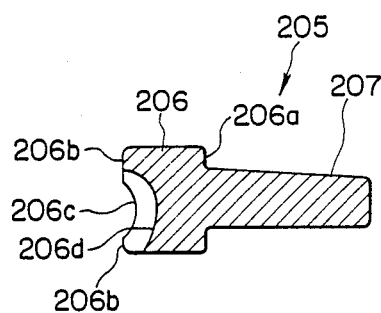
FIG. 10E is a sectional view taken along the line XE—XE of FIG. 10B.
Figure 10F:
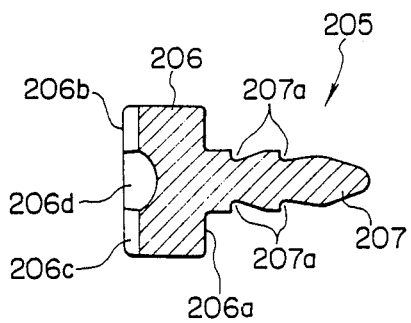
FIG. 10F is a sectional view taken along the line XF—XF of FIG. 10A.
Figure 10G:
FIG. 10G is a sectional view taken along the line XG—XG of FIG. 10A.

The first and second members 101 and 105 can be put together to form a finger joint as shown in FIGS. 7 and 8. Referring to FIG. 7, the first and second members 101 and 105 are put together in a straight line with the sliding portion 102 of the former engaging the sliding portion 106 of the latter. The second member 105 is shown in its longitudinal section. The protrusion 102c of the first member 101 is slidingly rotatably fitted in the concavity 106d of the second member 105. The outer surface 102b of the flexible portion 102 of the first member 101 contacts the outer surface 106b of the second member so that the protrusion 102c may be rotatable in the concavity 106d to vary the angle between the shank portions 103 and 107. The angle between the shank portions 103 and 107 is variable in a single plane of flexure until the surface 102d contacts the beveled surface 106c.

When the joint is bent, the surface 102b does not need to always be in contact with the surface 106b or 106c, but can be slightly spaced apart therefrom. It is sufficient to ensure that the surface 102b contacts the surface 106b when the first and second members lie in a straight line, and the beveled surface 106c when they have been moved to the maximum flexing limit of the joint. If the joint begins to flex in a wrong direction for some reason, the surface 102b is brought into contact with the surface 106b or 106c to correct the movement of the joint and cause it to flex only in a single plane.

Even if the surface 102b is always in contact with the beveled surface 106c and spaces the protrusion 102c apart from the wall of the concavity 106d, any lateral displacement of the first and second members 101 and 105 from each other can be avoided as soon as the protrusion 102c abuts on the wall of the concavity 106d.

FIG. 8 shows the first and second members put together and the shank portions 103 and 107 thereof set in the marrow of bones 111 and 112 respectively, in a finger. The joint is movable only in two directions. A ligament 113 connects the two bones 111 and 112 and causes the bones to urge the first and second members 101 and 105 against each other. Therefore, there is no possibility of the sliding portion 102 being separated from the sliding portion 106 resulting in the removal of the protrusion 102c from the concavity 106d. Moreover, the ligament 113 holds the joint in an appropriately assembled position until the shank portions 103 and 107 combine with the bones.

The artificial joint as hereinabove described is simple in construction and easy to manufacture. It is smoothly sliding only in two directions within an appropriate angle and is, therefore, a particularly suitable finger joint. As the two members forming the joint merely contact each other, it has a very high degree of strength and durability. It is very easy to assemble during any surgical operation, since it is sufficient to fit the protrusion 102c in the concavity 106d. Insofar as the protrusion 102c has a substantially hemispherical shape and the concavity 106d has a substantially hemispherical surface, they are smoothly slidable relative to each other.

When the second member 105 is placed near the tip of the finger, the force that is exerted by the tip of the finger is received on the center of the concavity 106d. Therefore, there is no possibility of the protrusion 102c being separated from the concavity 106d.

Because the walls of the triangular grooves 103a and 107a in the shank portions 103 and 107 are substantially perpendicular to the axes of the shank portions 103 and 107 and are also substantially perpendicular to the bones, the walls receive a substantially perpendicular force from the bones. This feature facilitates the growth of the bone tissue and promotes the connection of the shank portions with the bones. The walls need not necessarily be perpendicular to the shank portions, but can alternatively be formed to define an acute angle without causing any significant loss of the advantages as hereinabove described.

Referring now to FIGS. 9A to 12, there is shown an artificial joint according to a third embodiment of the present invention. It includes a first member shown by way of example in FIGS. 9A to 9F. The first member 201 comprises a sliding portion 202 and a shank portion 203. The sliding portion 202 has the shape of a rectangular parallelepiped that is rounded at each edge. It has an outer surface 202a projecting in a direction that is substantially perpendicular to the longitudinal axis of the first member 201. The shank portion 203 is joined to the surface 202b of the sliding portion 202 which is remote from its outer surface 202a. A protrusion 202c having a substantially semicircular cross section projects from approximately the center of the surface 202a in the direction in which the surface 202a projects, and partially surrounds the sliding portion 202.

The joint also includes a second member shown by way of example in FIGS. 10A to 10G. The second member 205 comprises a sliding portion 206 and a shank portion 207. The sliding portion 206 has the shape of a rectangular parallelepiped that is rounded at each edge. One of its largest surfaces, i.e., the surface 206a, is joined to the shank portion 207. The opposite surface 206b includes a curved surface 206c having a substantially semicircular cross section. The surface 206c extends longitudinally of the surface 206b, but has a longitudinal centerline deviating to some extent from that of the surface 206b. The surface 202b also includes a concavity 206d having a substantially semicircular cross section and extending at right angles to the curved surface 206c. The concavity 206d defines an arcuate surface lying substantially along the curvature of the curved surface 206c. When the first and second members are put together, the surface 202a of the first member 201 is capable of rolling on the curved surface 206c, while the protrusion 202c is slidingly rotatable in the concavity 206d.

Figure 11:
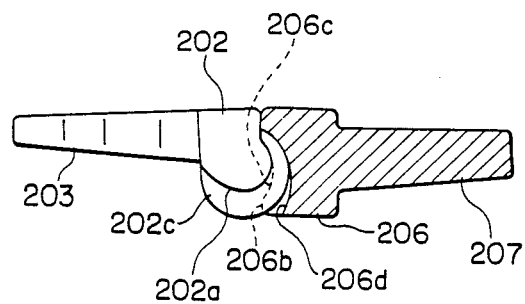
FIG. 11 is a view showing in its assembled form the joint according to the third embodiment of the present invention.
Figure 12:
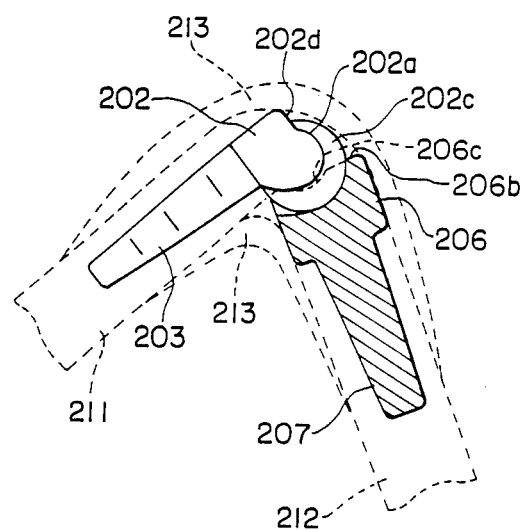
FIG. 12 is a view showing in its flexed position the joint of FIG. 11 attached to finger bones.

The first and second members 201 and 205 are put together to form a finger joint as shown in FIGURES 11 and 12. Referring to FIG. 11, they are put together in a straight line with the sliding portions 202 and 206 thereof contacting each other. The second member 205 is shown in its longitudinal section. The protrusion 202c of the first member 201 is fitted in the concavity 206d of the second member 205 and the surface 202a of the first member 201 contacts the curved surface 206c of the second member 205. If the surface 202a is rotated on the curved surface 206c so that the protrusion 202c may be rotated in the concavity 206d, the angle between the shank portions 203 and 207 can be varied in a single plane of flexure until the surface 202d or 202a of the sliding portion 202 of the first member 201 abuts on the surface 206b of the sliding portion 206 of the second member 205.

The surface 202a does not always need to be in contact with the curved surface 206c, but can be spaced apart therefrom to some extent. If the joint begins to flex in a wrong way for some reason or other, the surface 202a contacts the curved surface 206c to correct the movement of the joint so that it may flex only in two directions, or in a single plane.

Even if the surface 202b always remains in contact with the surface 206c and keeps the protrusion 202c spaced apart from the wall of the concavity 206d, any lateral displacement of the two members 201 and 205 from each other can be avoided as soon as the protrusion 202c abuts on the wall of the concavity 206d.

FIG. 12 shows the shank portions 203 and 207 set in the marrow of finger bones 211 and 212, respectively. The joint is slidable only in two directions. A ligament 213 connects the bones 211 and 212 and the bones 211 and 212 urge the members 201 and 205 against each other. Therefore, it is possible to avoid any separation of the slidable portions 202 and 206 from each other and thereby any resulting detachment of the protrusion 202c from the concavity 206d. The ligament 213 holds the joint in its appropriately assembled portion until the shank portions 203 and 207 combine with the bones.

The artificial joint as hereinabove described is simple in construction and easy to manufacture. It is smoothly slidable only in two directions within an appropriate angle and is, therefore, a particularly suitable finger joint. As the two members forming the joint merely contact each other, it has a very high degree of strength and durability. It is very easy to assemble during any surgical operation, since the only thing that has to be done is to form the joint to fit the protrusion 202c in the concavity 206d.

Although the surface 202a has been described as contacting the curved surface 206c, it is also possible to have it contact the surface 206b and thereby eliminate the curved surface 206c. There is no fear of the protrusion 202c detaching itself from the concavity 206d in which it is slidingly rotatable, insofar as the concavity 206d defines an arcuate wall surface. The concavity 206d can alternatively be formed to define a flat wall surface without giving rise to any possibility of the protrusion 202c being unintentionally separated therefrom, insofar as the surface 202a is slidingly rotatable in the curved surface 206c.

Although no specific material has been mentioned for making the artificial joint of the present invention, it is preferable to use ceramics, as they are non-toxic and readily combine with bone tissue that easily grows on ceramic surfaces. The use of a sintered product of $ZrO_2$ is, among other, preferred from the standpoint of mechanical strength and toughness. It is, however, sufficient to employ a ceramic material only on the surface of a joint. Therefore, it is practically advisable to coat the surface of a metal product with a ceramic material in order to produce an artificial joint of improved strength and durability.

The artificial joint of the present invention essentially comprises a first member adapted for attachment to a first bone and formed from a generally cylindrical body having a protruding middle portion and a second member adapted for attachment to a second bone and relative movement at a variable angle to the first member and having a concavity in which the protruding portion of the first member is slidably received. It is easy to manufacture and assemble. It is slidable only in two directions within an appropriate angle. It has a high degree of strength and durability.

It should be understood that the present invention is not limited to the particular embodiments described, but rather is susceptible to modifications, alterations, and equivalent arrangements within the scope of the appended claims.

What is claimed is:

1. An artificial joint for joining a first bone and a second bone comprising:

a first member having a first shank portion and a first slidable portion having a flat surface, said first shank portion comprising a tapered bar having a substantially square cross section with each corner rounded and including a first end adapted for attachment to the first bone, a second end, and a surface extending from said first end flush with and lying in the same plane as said flat surface of said first slidable portion, said first shank portion having said first slidable portion disposed at said second end, said first slidable portion having a substantially cylindrical shape and having a longitudinal axis that is substantially perpendicular to a longitudinal axis of said first shank portion; and a second member having (1) a second shank portion including a first end and a second end, said first end of said second shank portion being adapted for attachment to the second bone, and (2) a second slidable portion, having a shape substantially of a rectangular parallelepiped, disposed at said second end of said second shank portion, said second slidable portion having a surface opposite said second shank portion including an inwardly curved surface having its curve along its longer sides, said inwardly curved surface having a concavity complementary to and in sliding contact with an outer surface of said first slidable portion of said first member, said concavity being defined by an inner surface curved in a direction perpendicular to a direction of curvature of said inwardly curved surface and by a pair of outwardly deflected opposite edge surfaces.

2. An artificial joint according to claim 1, wherein a diameter of said first slidable portion of said first member is larger at a center than at each end thereof.

3. An artificial joint according to claim 2, wherein said concavity of said second member only partially covers the ends of said first slidable portion of said first member when said concavity is in contact with said first slidable portion.

4. An artificial joint according to claim 3, wherein an outer surface of said first slidable portion has a radius of longitudinal curvature that varies from a midpoint thereof to each end thereof.

5. An artificial joint according to claim 2, wherein an outer surface of said first slidable portion has a radius of longitudinal curvature that varies from a midpoint thereof to each end thereof.

6. An artificial joint for joining a first bone and a second bone comprising:
   a first member having (1) a first shank portion including a first end and a second end, said first end being adapted for attachment to the first bone, and (2) a first slidable portion disposed at said second end and including an outwardly protruding surface and a protrusion having a flat top surface projecting therefrom, said outwardly protruding surface having a diameter smaller than a diameter of said protrusion, and said protrusion protruding in a direction substantially parallel to a longitudinal axis of said first shank portion; and
   a second member having (1) a second shank portion including a first end and a second end, said first end being adapted for attachment to the second bone, and (2) a second slidable portion disposed at said second end of said second shank portion, said second slidable portion having a shape substantially of a rectangular parallelepiped including a face opposite said second shank portion having a beveled surface, said second slidable portion having a contact surface for contacting said protruding surface of said first slidable portion and a concave portion formed in said contact surface for receiving said protrusion of said first slidable portion.

7. An artificial joint according to claim 6, wherein said protrusion of said first slidable portion has a substantially hemispherical shape and said concave portion in said second slidable portion defines a substantially hemispherical wall surface.

8. An artificial joint according to claim 6, wherein when said protrustion of said first slidable portion is received in said concave portion of said contact surface of said second slidable portion, said first member and said second member are movable relative to each other in two directions through a specific angle.

9. An artificial joint for joining a first bone and a second bone comprising:
   a first member haivng (1) a first shank portion including a first end and a second end, said first end adapted for attachment to the first bone, and (2) a first slidable portion disposed at said second end, said first slidable portion having a shape substantially of a rectangular parallelepiped and having an outwardly protruding surface protruding in a direction substantially perpendicular to a longitudinal axis of said first mexber and a protrusion having a substantially semicircular cross section projecting therefrom in the direction in which said surface protrudes; and
   a second member having (1) a second shank portion having a first end and a second end, said first end of said second shank portion being adapted for attachment to the second bone, and (2) a second slidable portion disposed at said second end of said second shank portion, said second slidable portion having a shape substantially of a rectangular Parallelepiped and having a surface opposite said second shank portion including a curved surface, on which said protruding surface slides, having a substantially semicircular cross section extending longitudinally of said opposite surface and including a concavity, in which said protrusion slidably rotates, having a substantially semicircular cross section and extending at right angles to said curved surface.

10. An artificial joint according to claim 9, wherein when said protrusion of said first slidable portion is received in said concavity of said opposite surface of said second slidable portion, said first member and said second member are movable relative to each other in two directions through a specific angle.

* * * * *

UNITED STATES PATENT AND TRADEMARK OFFICE
CERTIFICATE OF CORRECTION

PATENT NO. : 4,685,919

DATED : August 11, 1987

INVENTOR(S) : Shigeo Niwa et al.

It is certified that error appears in the above-identified patent and that said Letters Patent is hereby corrected as shown below:

Claim 8, line 2, "protrustion" should be --protrusion--.

Claim 9, line 3, "haiving" should be --having--
line 11, "mexber" should be --member".

Signed and Sealed this

Ninth Day of February, 1988

Attest:

DONALD J. QUIGG

*Attesting Officer*      *Commissioner of Patents and Trademarks*